United States Patent [19]
Kumar

[11] Patent Number: 5,183,388
[45] Date of Patent: Feb. 2, 1993

[54] MOBILE HINGE MEMBER AND ORTHODONTIC APPLIANCE USING IT

[75] Inventor: Swadesh Kumar, Kongsvinger, Norway

[73] Assignee: Ortho-Dent, London, United Kingdom

[21] Appl. No.: 623,396

[22] PCT Filed: Apr. 3, 1990

[86] PCT No.: PCT/EP90/00523
§ 371 Date: Nov. 23, 1990
§ 102(e) Date: Nov. 23, 1990

[87] PCT Pub. No.: WO90/11731
PCT Pub. Date: Oct. 18, 1990

[30] Foreign Application Priority Data
Apr. 6, 1989 [NO] Norway .................................. 891420

[51] Int. Cl.$^5$ .................................................. A61C 3/00
[52] U.S. Cl. ................................................................ 433/19
[58] Field of Search .................. 433/13, 14, 18, 19, 433/22; 411/355, 356, 513

[56] References Cited

U.S. PATENT DOCUMENTS

| | | | |
|---|---|---|---|
| 711,948 | 10/1902 | Dodge | 411/513 X |
| 886,904 | 5/1908 | Wagner | 411/513 X |
| 1,525,408 | 2/1925 | Miller et al. | 411/513 |
| 1,761,581 | 6/1930 | Northey et al. | 411/355 X |
| 2,140,820 | 12/1938 | Summerhays | 411/513 |
| 2,383,068 | 8/1945 | MacLean, Jr. | 411/355 X |
| 3,357,292 | 12/1967 | Falkenberg | 411/355 |
| 4,462,800 | 7/1984 | Jones | 433/19 |
| 4,472,139 | 9/1984 | Rosenberg | 433/19 |
| 4,496,318 | 1/1985 | Connelly, Jr. | 433/14 |

FOREIGN PATENT DOCUMENTS 129955  3/1949  Sweden ...................... 433/18

Primary Examiner—Gene Mancene
Assistant Examiner—Nicholas D. Lucchesi

[57] ABSTRACT

An orthodontic appliance has a rod unit pivotally connected with arch wires by hinge members. The rod unit has bearing apertures at both ends. Each hinge member has a cylindrical shaft and a head on one end that is wider than the shaft and integrally former with the shaft. The shaft has an opening extending across its longitudinal axis. The shaft and the head are free of both outer and inner threads. The rod unit is pivotally connected with the arch wire by inserting the shaft of the hinge member into the bearing aperture and inserting the arch wire into the opening in the shaft.

3 Claims, 6 Drawing Sheets

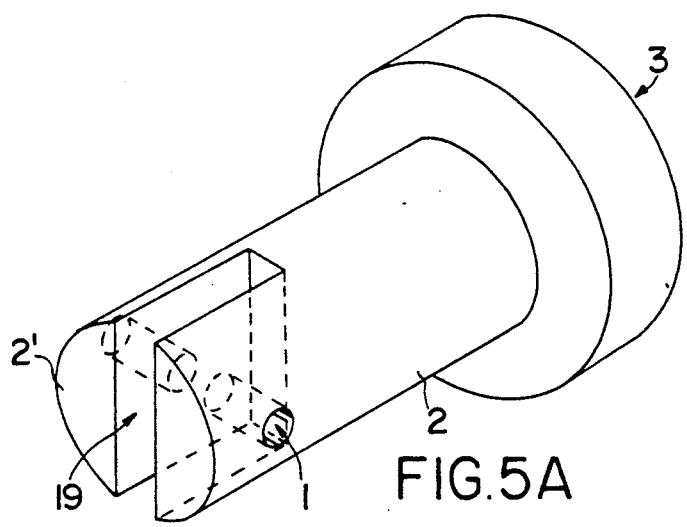
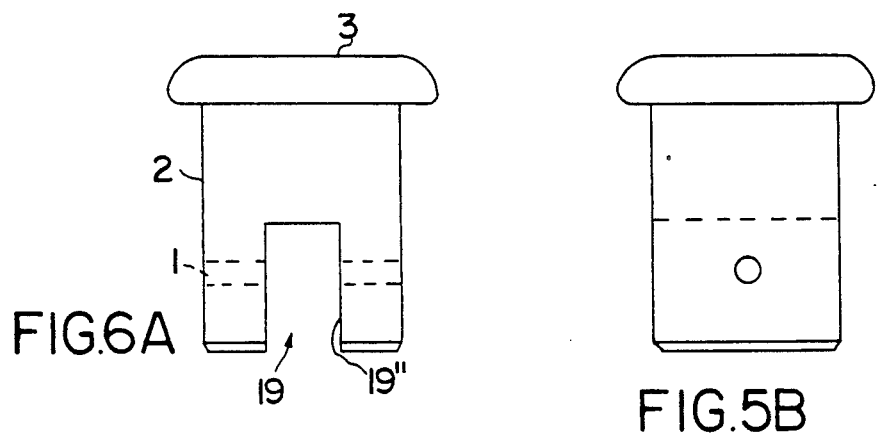
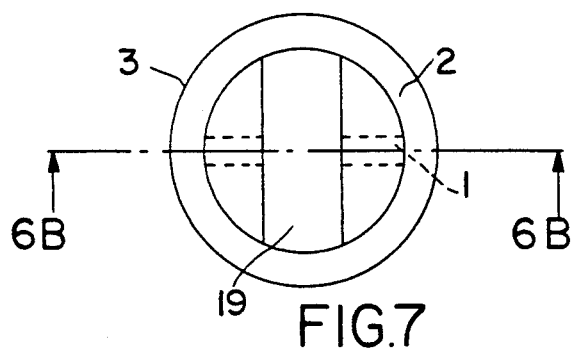
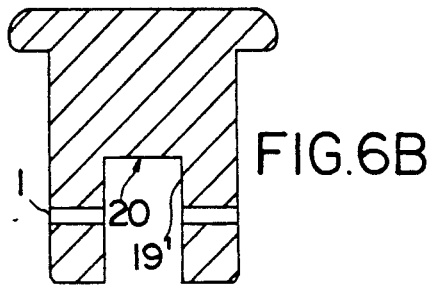

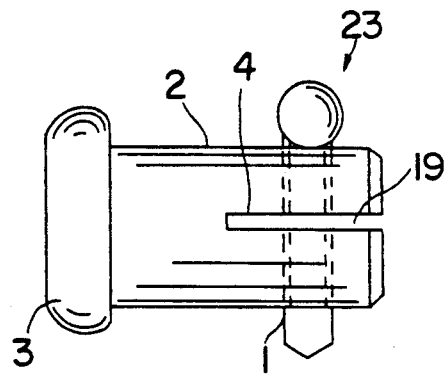
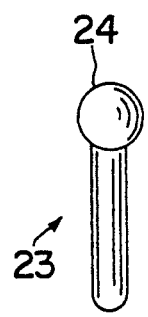
FIG.15  FIG.16
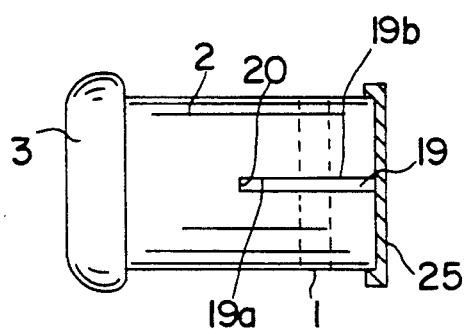
FIG.17
 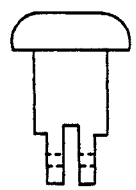
FIG.18A  FIG.19A
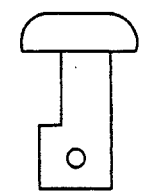 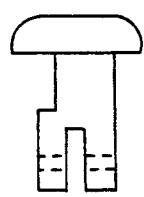
FIG.18B  FIG.19B
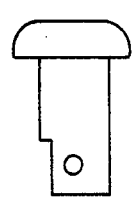 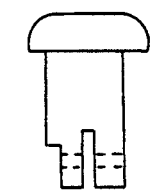
FIG.18C  FIG.19C

MOBILE HINGE MEMBER AND ORTHODONTIC APPLIANCE USING IT

This invention relates to a mobile hinge as used in orthodontic appliances where arch wires on the upper and lower jaw are interconnected by a rod unit that normally consists of two telescopically movable parts.

FIELD OF THE INVENTION

Previous designs for a telescopic unit and other accessories have been described in the following U.S. Pat. Nos.: 3,028,671 to Berger, 4,462,800 to Jones and 2,959,856 to Gurin. The Berger patent discloses slotted screw and a nut. The Jones patent employs a hinge-screw combination. The Gurin patent employs a hinge without collar but with set screw. Similar constructions can be derived from U.S. Pat. Nos. 2,959,856, 3,158,934, 3,238,619, 4,462,800, 4,551,095 and 4,795,342.

BACKGROUND OF THE INVENTION

All these hinges that are also commercially available have the disadvantage to use screws either to fasten the rod unit to the wire or to retain the hinge member in the bearing aperture of the rod unit. As the jaws move forward and backward, the screws have the tendency to become loose. If the screw is used to fasten the wire, another drawback consists in that the masticatory load, already under normal jaw movements, provides a tremendous amount of pressure acting onto the wire at the contact area with the screw, thus resulting in a metal fatigue and eventual breakage of the wire. The use of a screw implies also that very fine threads have to be manufactured which constitutes a relatively costly procedure. In many cases, the use of a screw results in a bulky construction which causes an irritation of the soft tissue. If the screw is connected to the wire, the lateral movement of the rod unit is restricted, thus increasing the patient's discomfort. Certainly, in U.S. Pat. No. 4,583,944 there is a hinge member consisting of a stud that is connected to a tube extending normally to its smaller shank. There is no screw and no separate part. However, such a design is not only bulky and, therefore, disagreable to the patient, but it is also difficult to manufacture, because the tube will usually be connected to the stud by soldering. Even if it were produced by other methods, it would always involve difficulties. Moreover, the telescopic unit of the Herbst appliance can only be stripped over the head portion of the stud, thus allowing that it can be stripped off by movements of the patient's jaws. Therefore, it never came into practice.

SUMMARY OF THE INVENTION

It is an object of the present invention to simplify the construction and to make it more reliable. Inconveniences to the patient should be avoided.

This object is achieved according to the invention by a movable hinge member in which a shaft portion of generally cylindrical shape is integrally formed with a head portion of larger width to retain the hinge member within the bearing aperture on one side, while it is retained by the wire itself or by a little pin on the other side. The wire may be inserted into the end opposite to the head portion by providing a hole or a slot that may be closed by suitable means. In this way, the connection with the wire may be effected in a surprisingly simple manner.

In principle, the head portion could be T-shaped; however, it is preferred to have it circular, when seen in the direction of the longitudinal axis of the shaft portion, because in this way, it is less irritating to the patient. For the same reasons, a cylindrical head can have at least one circular edge, especially on its front surface, rounded, whereby the front surface may outwardly be dished.

When a screw was used in known hinge members to retain it in the bearing aperture, it generally has an incision in its front surface for enabling insertion of a screw driver. Such incisions (or protrusions) are not only inconvenient for the patient, but it may also constitute a hygienic problem, since it may cause particles of food to be caught on. With a hinge member according to the invention, it is easily possible to form it free of incisions and/or protrusions.

BRIEF DESCRIPTION OF THE DRAWINGS

Further details of the invention will become apparant from the following description of embodiments according to the invention schematically illustrated in the drawings in which:

FIG. 1A to FIG. 4 represent the first embodiment of a hinge member used in the appliance according to FIG. 1, wherein FIG. 1A is a perspective view, FIG. 2 is a cross-section along the line II—II of FIG. 1B, FIG. 3 is a front end view from the side of the shaft portion, and FIG. 4 is a front end view from the head portion showing the course of the wire;

FIG. 5A to 7 are similar views, but of a second embodiment, where FIG. 5A is a perspective view, FIG. 5B is a lateral view, FIG. 6A is another lateral view, when the hinge member is turned by 90° about its longitudinal axis with respect to FIG. 5B, FIG. 6B is a crossection along the line B—B of FIG. 7 which is a bottom view to FIG. 6A;

FIGS. 15 to 19 illustrate alternative possibilities to ensure retaining of the arch wire with an embodiment according to FIGS. 5A to 7.

FIG. 20A shows a variation of the appliance of FIG. 5A;

FIG. 20B shows an application of such appliance, connected with an appliance according FIG. 1A.

DETAILED DESCRIPTION OF THE DRAWINGS

Figure 1:
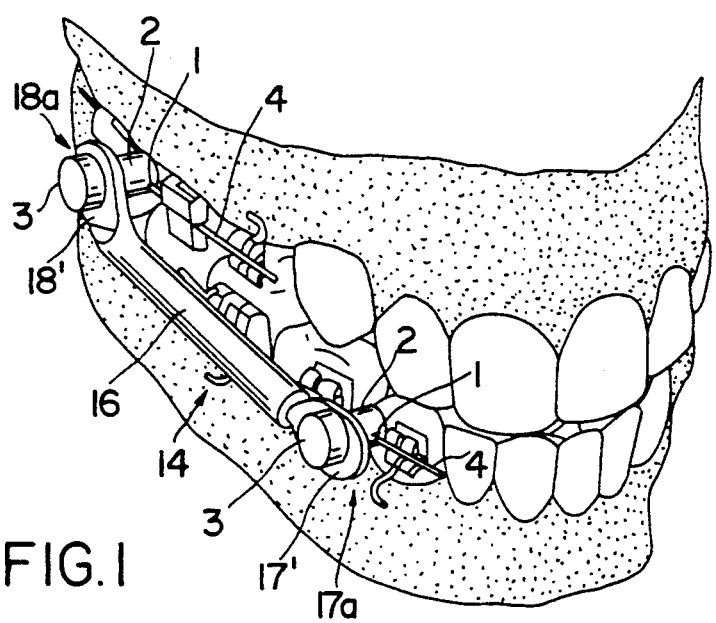
FIG. 1 is a perspective view of human jaws with an orthodontic appliance according to the invention in a first embodiment.

FIG. 1 shows a orthodontal appliance according to the invention in practical use. On a telescopic rod unit 14, there are bearing forming elements 17a and 18a on each end. Each of the elements 17a, 18a, has a buccal surface 17' and 18' while the flat elements 17a, 18a have a surface 17" and 18" on the side facing the respective tooth, as will become apparant from FIG. 14. Each element 17a, 18a has a bearing aperture 17 and 18 in it to receive a movable hinge member 1, 2 and 3.

Figure 14:
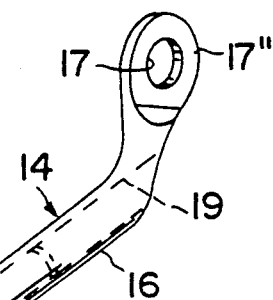
FIG. 14 is a perspective view of a usual telescopic rod unit.

From FIG. 14, it will clearly be seen that the rod unit 14 generally consists of two parts 15 and 16, the latter receiving the part 15 by sliding engagement within a bore 19. This is the usual structure of a so called Herbst appliance. The invention, however, is by no means restricted to such a telescopic form of a rod unit and may be used with any kind of rod units whatsoever.

The movable hinge members of FIG. 1 consist of a shaft portion 2 ending on the buccal side in a head portion 3 that is integrally formed with it, as may clearly be seen from FIGS. 1A to 4. Thus, it is no longer necessary to screw it onto the shaft portion, as it was common heretofore, which operation is complicated to do and implies the danger that the screw can get lost and could be swallowed by the patient. Moreover, such screws have the tendency to become loose due to the movements of the jaws, thus entraining the same risk.

FIGS. 1, 1B, 2 and 4 show also that the head portion has neither incisions nor protrusions, as was necessary with screws. This prevents irritations of the soft tissues of the patient and avoids that particles of food could remain in it. From FIGS. 1B and 2 it will clearly be seen that the head portion 3, according to a preferred embodiment, is not only generally cilincrical, but has also its circular outer edge 3', which looks away from the shaft portion 2, rounded so that the head portion 3 has a front surface 3" is slightly outwardly dished. This dished front surface looks preferably to the buccal side (FIG. 1) because it doesn't provoke any irritation of the tissues, especially if made of stainless steel. Thus, the head portion engages in this preferred form the buccal surface 17' or 18' of the rod unit 12.

Figure 1A:
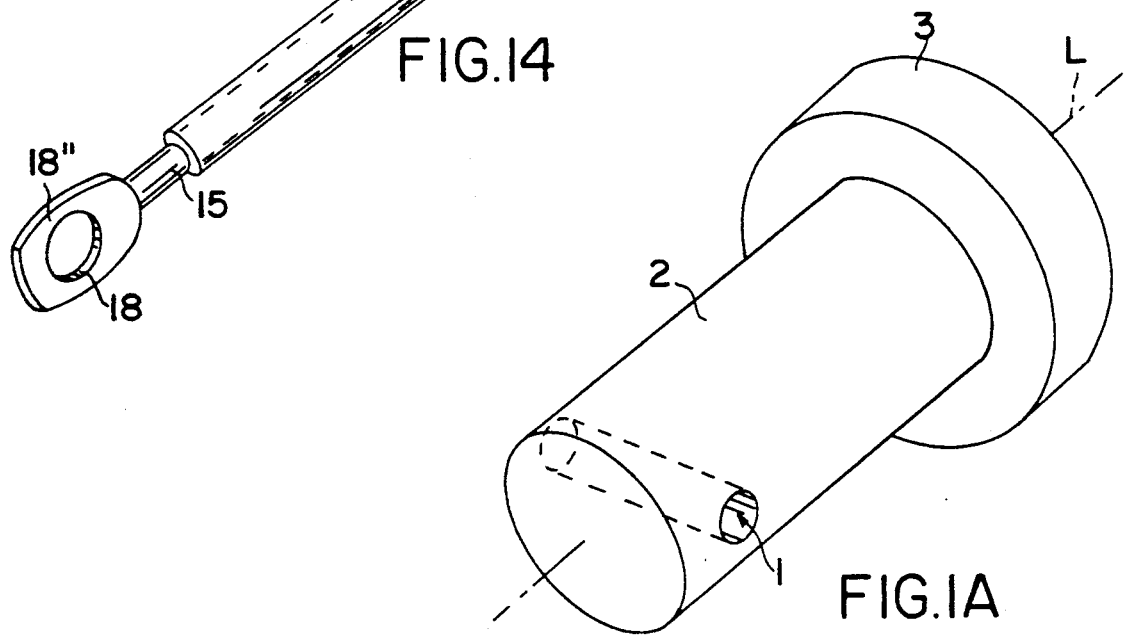
Figure 2O:
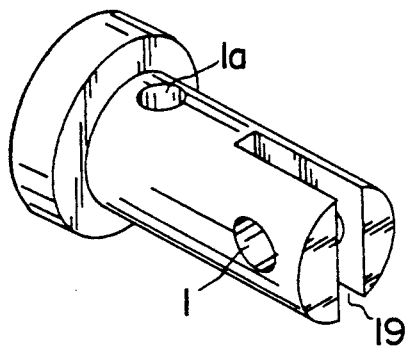
Figure 1B:
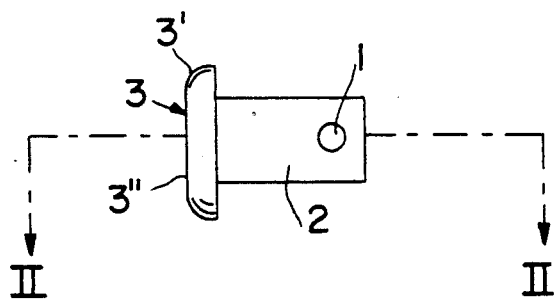
FIG. 1B is a lateral view.
Figure 2:
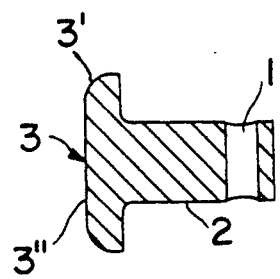
Figure 2O:
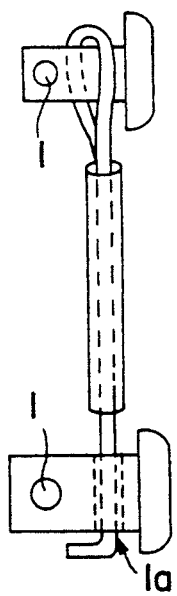
Figure 3:
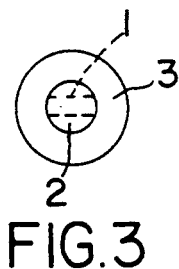
Figure 4:
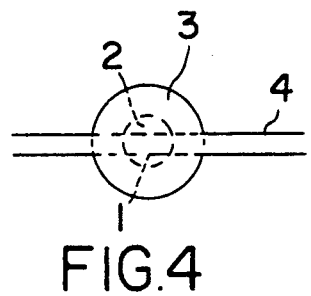
Figure 8A:
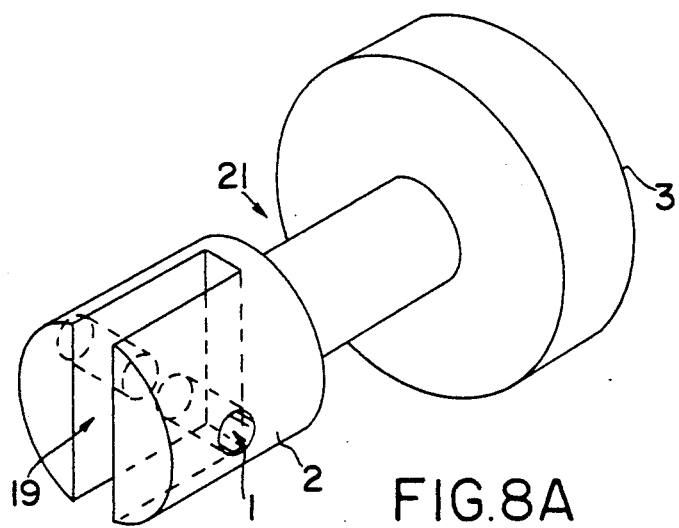
FIGS. 8A to 10 are representations of a third embodiment in similar views as in FIGS. 5A to 7, and so are FIGS. 11A to 13 depicting a fourth embodiment.
Figure 9A:
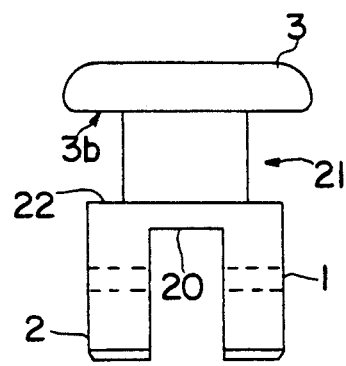
Figure 8B:
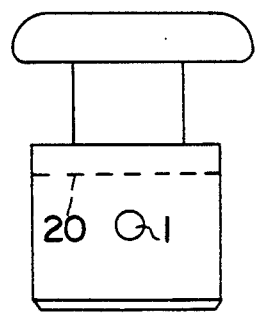
Figure 10:
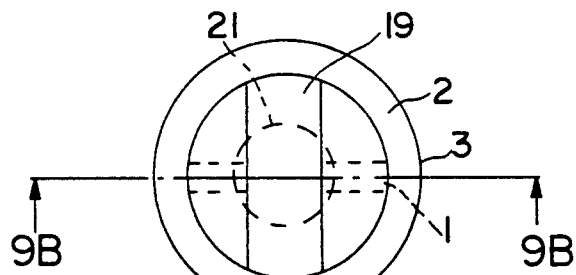
Figure 9B:
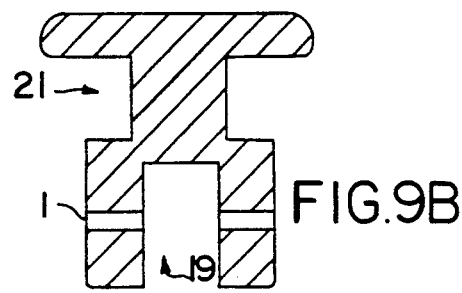
Figure 11A:
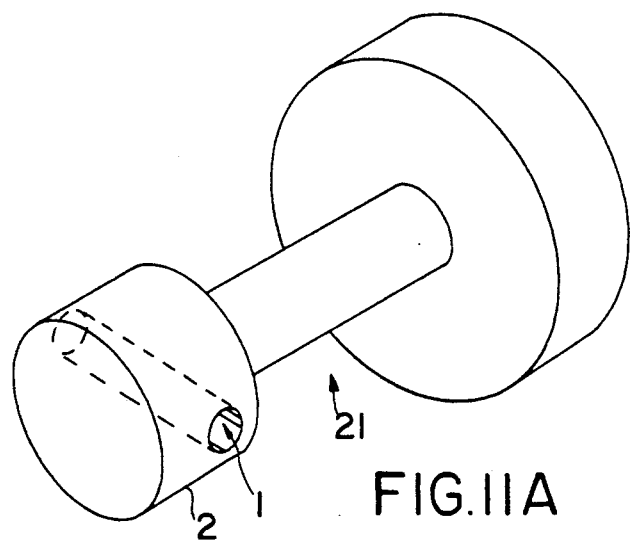
Figure 12A:
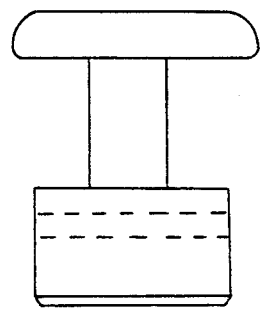
Figure 11B:
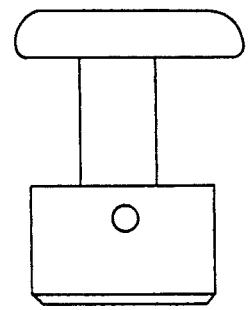
Figure 13:
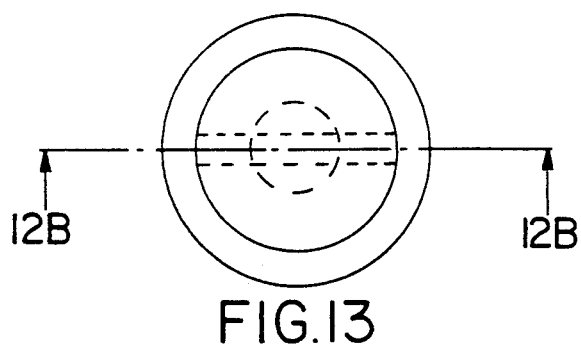
Figure 12B:
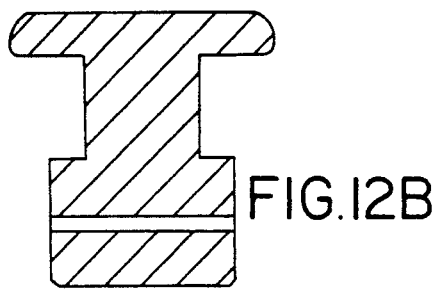

In order to ensure retention of the movable hinge member 1-3 within the respective aperture 17 or 18, there is a bore 1 arranged at the area of the other end of the shaft portion 2, opposite to the end carrying the head portion 3. As best seen in FIG. 1A, the hole 1 extends across the longitudinal axis L of the hinge member and preferrably at right angles. This hole serves to receive the wire 4 (FIG. 4) which can be fastened on it in any way desired. In most cases, it will be sufficient to bend the end of the wire around the end of the shaft portion 2. But it would also be possible to use clamping pieces to be clamped onto the wire, e.g. on both sides of the hole 1. Thus, the arch wire 4 itself retains the hinge member 1-3 within the respective aperture 17 or 18. The wire 4 is no longer clamped by any screw and can, if necessary, move with less friction within the hole 1. Thus, metal fatigue and breakage of the wire 4 are easily avoided, while the hinge member can move with a greater amount of play.

While stainless steel has been mentioned as a possible material for the hinge member 1-3, also medical grade plastic material can be used.

When mounting the appliance of FIG. 1, it is sufficient to insert the hinge members 1-3 into the apertures 17 and 18 of the rod unit 14, the head portion 3 acting as a limiting collar. Then, the wire is inserted into the holes 1 of both hinge members before it is ligated to the usual brackets in the oral cavity.

Especially when an arch wire with a square cross-section is used, known under the brand name "COBRA" arch wire, it may be useful to apply an embodiment, as represented in FIGS. 5A to 7. In this embodiment, in addition to the arrangement described with reference to FIGS. 1A to 4, there is a slot-like incision 19 which extends diametrally of the shaft portion 2 and from the end surface 2' of the latter inwardly across the course of the hole 1, preferably at right angles. FIGS. 5B and 6A show that the head portion 3 has both outer circular edges rounded. In this embodiment, the arch wire can be inserted into the slot 19 to extend diametrally to the shaft portion 2 and can be retained by inserting a pin or plug into the hole 1. Alternatively, the hole 1 may be used to insert an arch wire of circular cross-section.

This embodiment allows the wire to move more freely, thus increasing the comfort to the patient. It is, however, suitable that the dimensions of the slot-like incision 19 meets approximately the dimensions of the cross-section of the wire either with its bottom surface 20 and the hole 1 (when a pin is inserted) and with the lateral surface portions 19', or with the hole 1 and the outer surface portions 19" (FIG. 6A), as will described later with reference to FIG. 17, or both.

An alternative embodiment may be derived from FIGS. 8A to 10. In this embodiment, the shaft portion 2 has an annular recess 21 adjacent the head portion 3. In addition, the slot-like incision 19 may be provided or may also be omitted. The annular recess 21 provides a collar which after insertion into a bearing aperture 17 or 18 (FIG. 14) serves as a bearing surface, since the bearing forming element 17a or 18a will lie between the inner surface 3b of the head portion 3 and the collar surface 22 in front of it (FIG. 9A). Thus, the arch wire being mounted on the end portion of the shaft or shank 2 will become free of any motion that will occur during movements of the jaws, thus contributing to a better and more durable seat of the wire in the brackets on the teeth.

A similar construction as in FIGS. 8A to 10, but without the slot-like incision 19, is shown in FIGS. 11A to 13. Such an arrangement is, above all, intended for wires of circular cross-section, but it will be understood that in principle, it would also possible to insert a wire of a square cross-section into the hole 1, if it is large enough. It should also be noted that the expression "arch wire" in this context should encompass all elongated structures that would be intended and used for orthodontic appliances for the purposes of an ordinary arch wire.

FIG. 15 illustrates the use of a hinge member according to FIGS. 5A to 7 in practice. If one inserts a pin or plug 23 into the hole 1, the slot 19 is closed to retain a wire 4 in it. The wire 4 has much more freedom to move and is less clamped than heretofore so that tendency of breakage is reduced and mobility of the jaws is improved. The pin or plug 23 is preferably slightly conical, as is best seen from FIG. 15 in relation to the hole 1. If the pin 23 consists of relatively soft material, such as plastic material (e.g. polyurethane), it may be depressed into the hole, until its upper part deforms elastically. To this end, it may be advantageous to give the pin 23 a cross-section that deviates from a circular one, as to provide sharp edges which are easier deformed within the hole 1. For example, a star-like cross-section could be provided. On the other hand, the head 24 of the pin 23 could assume any shape desired. It could be favourable to provide a shape that fits exactly with the surface of the shaft 2, i.e. a T-shape, but with a curved cross-beam snugly engaging the peripheral surface of the shaft portion 2.

In the case of FIG. 17, the slot 19 is closed by a front cap 25 which is welded, soldered or fixed in any suitable way to the front surface of the shaft portion 2. Thus, the hole 1 could, in principle, be omitted. But if it is required that the dimensions of the slot 19 conform essentially to the dimensions of the arch wire within a first section 19a reaching from the surface 20 until the hole 1, or in a section 19b extending from the hole 1 til the cup 25, it could be advantageous to provide a different length of the sections 19a and 19b to conform to different types of wires. Thus, as shown, the hole 1 intersects the slot 19 to form slot sections 19a, 19b of different lengths.

FIGS. 18 and 19 show that the recess need not be annular and could likewise be arranged adjacent to the second end of the shaft portion (FIGS. 18A and C, 19A and C). Also in this case, the arch wire is released from forces acting upon it when the jaws move.

While the hinge member has been described in its preferred realization, i.e. being integrally formed with the shaft portion, it will be understood that it would likewise be possible to manufacture them as two separate parts which afterwards are interconnected to one another. This could be done by providing one of these parts with a bore and the other one with a fitting projection that is placed within the bore, the interconnection being effected either by providing snapping means (which connect both parts inextricably) or by pressing on, by cementing on, or even by providing respective threads (which, in this case, wouldn't provoke the disadvantages discussed above in relation with screws acting upon the wire or on the soft tissues, since no incision would be necessary for assembling both parts during manufacture).

It should further be noted that the hole—either for receiving the arch wire 4 or the plug 23—need not to be circular in cross-section. This will be easily understood when considering the slot 19, which is rectangular in cross-section for receiving rectangular or square-shaped wires. There is still more constructive freedom in relation with the pin or plug 23 which also may be triangular in cross-section or may have any other shape. Accordingly, the hole 1 may have any cross-section desired.

Furthermore, the head 3, in its preferred embodiment, is larger in width or diameter than the shaft portion 2. However, for some embodiments it could be desirable to make it smaller, although retaining of the shaft portion, in this case, has to be attained in another way; for example, the head of smaller diameter could have a hole similar to the hole 1 in order to receive a plug 23 which then will play the role of the head 3, as shown. One could also solder (or otherwise connect) a round or square tube to the end of the shaft portion 2 so as to extend normally to its longitudinal axis L. Especially silver would be suitable for soldering. Such a design could also be used for providing the hole 1 at the second end of the shaft portion. It has already been mentioned in the introduction that the head need not to be cylindrical, but can be T-shaped. Other possible shapes are spherical or cup-shaped.

Although hinge members with a single hole 1 on the free end of the shaft portion 2 have been shown, it could, for some applications, likewise be provided with at least another hole near the head 3.

Such an embodiment is shown in FIGS. 20A, 20B where besides the hole 1 there is another hole 1a near the head portion 3. This hole 1a could extend in the same plane and direction as the hole 1, but extends preferably in a deferring plane, especially a plane normal to the one of hole 1. The purpose of the hole 1a may be to connect some wire parts of the Herbst appliance with one of the hinges.

I claim:
1. An orthodontic appliance comprising
   a rod unit having two ends;
   a pair of bearing aperture forming means each connected to one of said ends, said bearing aperture forming means having a buccal surface and a tooth facing surface;
   at least one hinge member to be received in one of said bearing aperture forming means, said hinge member including a substantially cylindrical shaft portion having a predetermined diameter, and a first end and a second end along a longitudinal axis;
   head means on said first end, being larger in width than said predetermined diameter of said shaft portion when measured in normal direction to said longitudinal axis, said head means being integrally formed with said shaft portion; and
   at least one opening within the range of said second end, said at least one opening extending across said longitudinal axis of said shaft portion;
   said shaft portion and said head means being free of both inner and outer threads so as to enable connection with said rod unit by inserting said shaft portion into said bearing aperture forming means and retaining said shaft portion by inserting a wire into said at least one opening.
2. An appliance as claimed in claim 1, wherein said head means faces said buccal surface.
3. An orthodontic appliance comprising
   a rod unit pivotally connected with an arch wire by at least one hinge member;
   said rod unit having two ends, and
   a pair of bearing aperture forming means each connected to one of said ends, said bearing aperture forming means having a buccal surface and a tooth facing surface;
   said at least one hinge member being inserted into one of said bearing aperture forming means;
   said at least one hinge member including a substantially cylindrical shaft portion having a predetermined diameter and a first end and a second end along a longitudinal axis;
   head means on said first end that is larger in width than said pre-determined diameter of said shaft portion when measured in normal direction to said longitudinal axis, said head means being integrally formed with said shaft portion; and
   at least one opening within the range of said second end, said at least one opening extending across said longitudinal axis of said shaft portion;
   said shaft portion and said head means being free of both outer and inner threads, whereby said rod unit is pivotally connected with said arch wire by merely inserting said shaft portion into said bearing aperture forming means and retaining said shaft portion therein by inserting said arch wire into said at least one opening.

* * * * *